United States Patent [19]
Wright

[11] Patent Number: 5,338,674
[45] Date of Patent: Aug. 16, 1994

[54] PROCESS FOR PRODUCING A VACCINE FOR A PATHOGENIC RNA VIRUS AND PRODUCT THEREOF

[76] Inventor: Stephen E. Wright, 2111 Lakeline Dr., Salt Lake City, Utah 84109

[21] Appl. No.: 914,620

[22] Filed: Oct. 2, 1986

Related U.S. Application Data

[63] Continuation of Ser. No. 469,985, Feb. 25, 1983, abandoned.

[51] Int. Cl.$^5$ ............... C12N 15/09; A61K 39/12
[52] U.S. Cl. ................... 435/172.3; 424/199.1; 424/207.1; 424/816; 424/235.1
[58] Field of Search ............ 435/68, 70, 172.3, 235, 435/948, 68.1, 235.1, 70.1; 424/89

[56] References Cited

U.S. PATENT DOCUMENTS 4,593,002  6/1926  Dulbecco .................. 435/172.3
4,603,112  7/1986  Paoletti et al. .............. 435/235

OTHER PUBLICATIONS

Cohen, J., Science, Nov. 1, 1991, p. 647.
Berman, P., et al., Nature, 345, 622–625 (1990).
Elliott, T., et al., Nature, 348, 195–197 (1990).
Winner, E., JPOS, Sep. 1988, pp. 608–615.
Girard, M., et al., PNAS USA, 88, 542–546 (1991).
Groopman, J., Nature, 349, 568–569 (1991).
"Dictionary of Biochemistry", J. Stenesh, p. 330 (1975).
Matthews et al., "Prospects for Development of a Vaccine Against HIV", pp. 313–325, Human Retroviruses, Cancer and AIDS.
Fujita et al., J. Virol., vol. 27(3), pp. 465–474 (1978).
Pagatsch et al., J. Virol., vol. 43(2), pp. 503–510 (1982).
Hughes, J. Viol., vol. 43(1), pp. 191–200 (1982).
Robinson et al., Chem. Abst., vol. 78(5), No. 26160n (1972).

*Primary Examiner*—Richard A. Schwartz
*Attorney, Agent, or Firm*—Mallinckrodt & Mallinckrodt

[57] ABSTRACT

A process for producing live, non-pathogenic, vaccines for the pathogens RNA turmor virus utilizes gene-altering technology to produce an altered genome which codes for the antigenic determinants of a pathogen, but has no genes coding for pathogenicity. The vaccine is the phenotypic expression of the altered genome. Specifically, an avian RNA tumor virus env gene is cloned into the non-pathogenic RNA virus RAV-O and the resulting recombinant product is replicated in host cells to provide a recombinant vaccine for the pathogen avian RNA tumor virus.

4 Claims, 1 Drawing Sheet

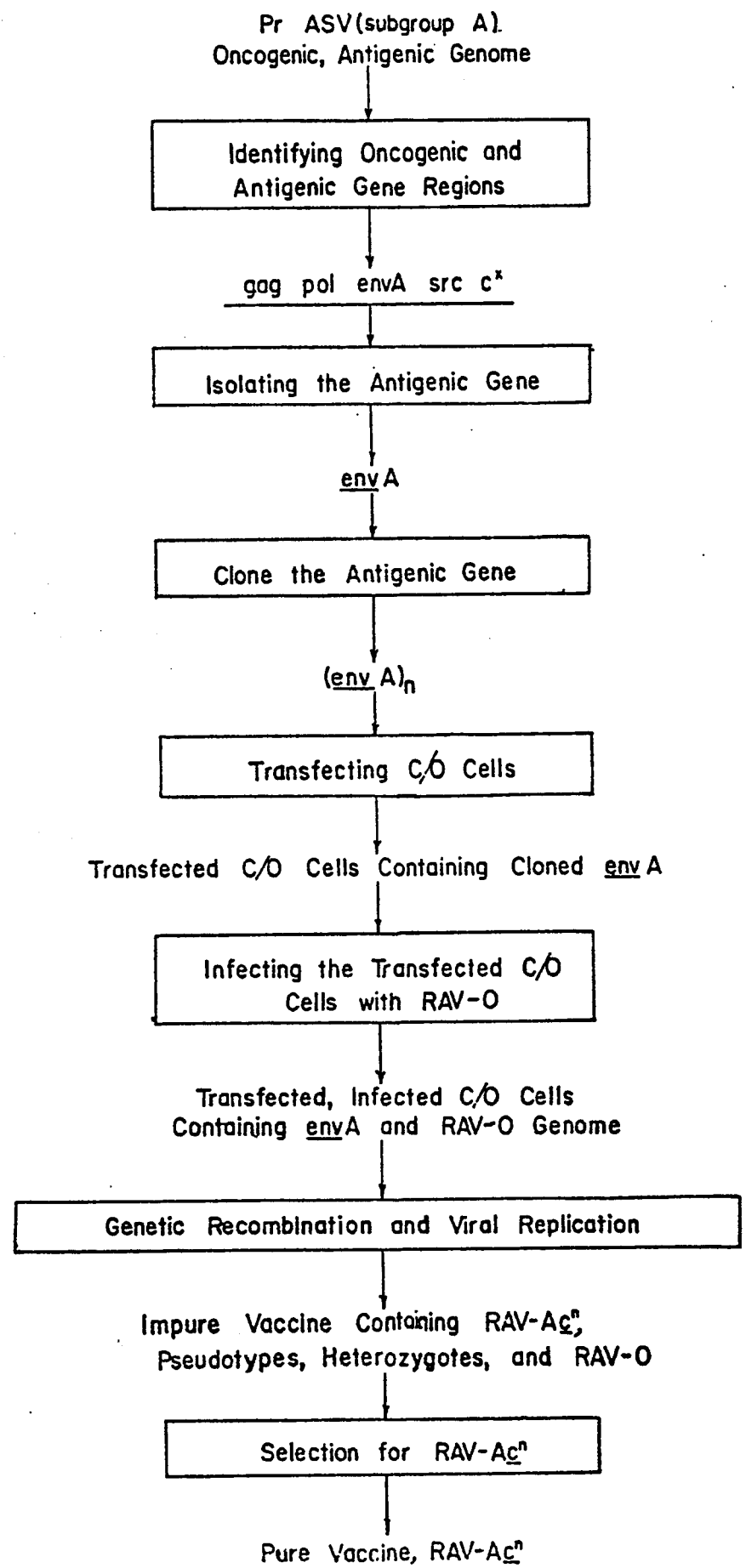

PROCESS FOR PRODUCING A VACCINE FOR A PATHOGENIC RNA VIRUS AND PRODUCT THEREOF

PRIOR APPLICATION

The present application is a continuation of an application filed Feb. 25, 1983, Ser. No. 469,985, entitled "METHOD FOR PRODUCING A VACCINE AND PRODUCT THEREOF", now abandoned.

BACKGROUND OF THE INVENTION

1. Field:

The invention relates to processes for producing vaccines against pathogens and to the vaccines produced thereby. For the purpose of this invention, a pathogen includes but is not limited to disease-causing organisms, viruses, some normal cells, abnormal cells, and any products or parts thereof.

2. State of the Art

In general, a vaccine is any material which induces an organism to acquire immunity against disease. Effective vaccines work by triggering an organism's normal immunological responses against a disease, but, at the same time, do not themselves cause the disease. In other words, a vaccine will typically have the antigenic determinants of a pathogen, but not the pathogenic properties. Once on organism's immunological responses against a disease are triggered, the organism starts producing disease-fighting agents. When the titer of disease-fighting agents reach a certain level, the organism acquires an immunity against the disease.

Many forms of vaccines against viral-caused diseases have been used. The most efficacious virus vaccines have been developed by attenuating disease-causing viruses. For example, attenuation of the Marek's disease virus (MDV) has worked as vaccine for chickens. In humans, attenuated polio and measles viruses have worked as vaccines.

Studies on oncogenic viruses in animal systems have been done. Some attenuated oncogenic viruses have been found to immunize, while other fail. The use of killed avian sarcoma virus as a vaccine has been shown to be ineffective in preventing tumors in chickens. In the murine RNA tumor virus system, however, immunization of mice with an inactivated leukemia virus prevented leukemia when challenged with the same live virus, and formalin-killed mammary tumor virus afforded some protection from challenge by the live virus.

Attenuated viruses have been used as a vaccine in the murine leukemia virus system. It was found that live, non-oncogenic murine leukemia viruses, when inoculated into newborn mice, protected the mice from development of leukemia after challenge with highly oncogenic Gross leukemia virus. Cells infected by non-oncogenic, yet antigenic, murine leukemia viruses also protected the animal from tumors produced by the virulent parent virus. Similar studies have been conducted with the radiation leukemia virus. The thymotropic radiation leukemia virus appears to lose its oncogenicity when grown in tissue culture on fibroblasts, yet still retains its antigenicity. Mice were successfully immunized with this attenuated virus. It also has been shown that the radiation leukemia virus can protect an animal from radiation-virus-induced lymphoma cells. Likewise, a benign bone tumor virus protects against a malignant bone tumor virus cancer induction. Immunization with infectious avian leukosis virus has also rendered chickens resistant to tumor development on challenge with avian sarcoma virus. Successful results have been obtained by immunizing against virus-induced leukemia by leukemic cell suspension. Avian leukosis viruses, used as live vaccines, have been shown to protect animals in vivo from sarcomagenesis. It has been shown that the avian and murine leukosis virus of different subgroups can protect an animal from tumor virus induced tumorigenesis. A particular murine leukemia virus in the Friend virus complex has been shown to cause spontaneous regression of the leukemia.

The major drawback with using an attenuated, disease-causing virus as a vaccine is the possibility that a small percentage of the vaccine will not be attenuated and that, therefore, the vaccine will induce the disease instead of immunity upon vaccination. This is especially a problem with vaccines against oncogenic viruses, because none of the attenuated viruses have been shown to be deleted of the oncogenic gene regions and, thus, all are potentially oncogenic. Furthermore, naked deoxyribonucleic acid (DNA) cannot be used as an antigen since it has been shown to produce malignant tumors in vivo. In addition, enhancement of tumorigenesis was noted in two carcinogenesis systems and in one murine sarcoma virus system where an attenuated virus was the vaccine. Another problem with attenuated virus vaccines is that the attenuation involves single nucleotide base changes which can and have reverted back to the pathogen.

Other types of vaccines have been developed by vaccinating with material which has the same or similar antigenic properties of a pathogen. Having the same antigenicity as the pathogen, the material will trigger an immunological response which will immunize against the pathogen. For example, the turkey herpes virus (HVT) is used as a vaccine against Marek's disease, and subunit vaccines have also been successful. The problems with these types of vaccines are numerous. First, it is often difficult to identify and isolate a material with the same antigenic properties as the pathogen, and subunits are difficult to obtain in large quantity. Further, such material may induce a cross-immununity for non-disease-causing agents or substances which are beneficial to the immunized organism.

SUMMARY OF THE INVENTION

Objective: In the making of the invention, it was an objective to provide a process of producing a vaccine against a pathogen, the vaccine having the antigenic determinants of the pathogen, but no pathogenic properties.

Features: In the accomplishment of the foregoing objective of the invention, the process of making the vaccine utilizes gene-altering technology to produce a vaccine which has the antigenic determinants of a pathogen, but no pathogenic properties. The vaccine is structured such that its genome possesses genes which code for the antigenic determinants of the pathogen, but has no genes for pathogenic properties. The resulting vaccine will trigger the immunological responses of an organism, but, at the same time, will have zero percent chance of inducing disease during vaccination. The resulting immunological responses of the organism will provide the organism with immunity against the pathogen.

THE DRAWING

The single FIGURE of the drawing is a flow sheet representing the process of the invention as applied to the production of an avian RNA tumor virus, the particular steps shown representing the best mode presently contemplated for carrying out the process as so applied.

DETAILED DESCRIPTION OF THE SPECIFIC EMBODIMENT

According to the invention, a vaccine is produced which possesses a pathogen's antigenic determinants, but does not possess any pathogenic properties. The pathogen may be any disease-causing entity as previously defined; typically, such pathogens include bacteria, fungi, parasites, viruses, and abnormal cells such as malignant or other disease-producing cells.

The first step in the process of production of a vaccine is identification of gene regions in the pathogen which code for the antigenic determinants and the pathogenic properties. Once those regions have been identified, the second step, gene alteration, is performed to produce a genome which codes for the antigenic determinants of the pathogen, but no pathogenic properties. In the third step of the invention, an expression of the genome is obtained.

Identification of the antigenic and pathogenic gene regions may be accomplished by a number of standard techniques. Such standard techniques include but are not limited to hybridization including hybrid-arrested translation and hybrid-selected translation; marker rescue of different gene regions; transformation with different gene regions; gene mapping by hybridization and oligonucleotide localization; mutation with complementation; and gene or gene product sequencing.

Gene alteration may be accomplished by a number of standard techniques. Such standard techniques include but are not limited to gene deletion, mutagenesis, gene addition, and gene exchange.

Gene deletion may be used to accomplish gene alteration. Gene deletion may be effected with gene splicing by using at least one suitable restriction enzyme to cut out the previously identified pathogenic gene region from the pathogen's genome, while at the same time not altering the previously identified antigenic gene region. After the pathogenic gene region is removed, the remaining gene regions are put back together with an appropriate ligase to form the genome of the vaccine. In another form of this technique, a gene-deleting agent is used to induce deletion of the pathogenic gene regions in vivo or in vitro, and the remaining regions are allowed to recombine to form the genome of the vaccine.

Mutagenesis may be used to accomplish gene alteration. Mutagenesis is changing of gene regions by exchange, addition, deletion or alteration of at least one nucleotide base, and may be effected by a number of standard techniques, including but not limited to gene splicing and treatment with mutagenic agents. To produce the genome of the vaccine, the previously identified pathogenic gene region of a pathogen is mutated to become non-pathogenic, or a non-pathogen's antigenic gene region is mutated to code for the previously identified antigenicity of a pathogen.

Gene addition may be used to accomplish gene alteration. Gene addition may be effected with gene splicing by using an appropriate restriction endonuclease and ligase to insert the previously identified antigenic gene region into a non-pathogenic genome to form the genome of the vaccine. Gene addition may also be effected by transformation with DNA or a vector. If the gene addition is effected by a vector, incorporation of the gene into the host genome may or may not be required for transformation. Vectors may include viruses which will introduce the sequences to be added by infection.

Gene exchange may be used to accomplish gene alteration. Several different standard techniques of gene exchange, including but not limited to genetic recombination and marker rescue, may be used to effect gene exchange. In the technique of marker rescue, the previously identified antigenic gene regions are rescued from a host cell with a non-pathogenic virus. The resulting virus will possess the genome of the vaccine. Genetic recombination may be used to form the vaccine genome by in vivo naturally occurring recombination or by in vitro recombination using a vector, such as recombinant plasmid DNA introduced into bacteria.

An expression of the vaccine genome which is produced from the gene alteration step, is obtained to produce the vaccine. Techniques to accomplish expression differ, depending on whether the vaccine genome is produced in vivo or in vitro. Expression of an in vivo derived genome is effected by permitting the genome to replicate to produce the vaccine. Expression of an in vitro derived genome may be effected by a number of standard techniques, including but not limited to transformation and transfection. For example, vaccine genomes derived from organisms or cells are expressed by transforming an appropriate host with the vaccine genomic DNA to produce the vaccine. For vaccine genomes derived from viruses, expression is by transfection of an appropriate host with the genetic material to produce the vaccine. In another expression technique, a non-pathogenic virus may be used to marker rescue antigenic genes from pathogens other than viruses to obtain a vaccine.

When using many of these techniques, the expressed vaccine is often difficult to produce and physically recover, because a limited amount of the previously identified antigenic and pathogenic gene regions are available. To reduce these technical difficulties, cloning of these gene regions may be done to produce large quantities of such regions, which may then be used in the production of the vaccine. This results in the expression of a large quantity of vaccine, which is easier to recover than a small amount.

The process often produces a combination of resulting genomes. The genomes result in a multiplicity of expressions, only one of which will induce the correct immunological responses to produce immunity against the pathogen. For example, the possible genomes produced by marker rescue may be expressed as four types of virus particles. First, there is the genetic recombinant, which is a viral particle having the genome of the rescuing non-pathogenic virus, except that the normal envelope gene has been replaced with the antigenic gene of the pathogenic agent. Second, there is the pseudotype, which is a viral particle having the complete genome of the rescuing non-pathogenic virus and the physical antigenicity of the pathogenic agent, but not the genes which code for the antigenicity. Third, there is the heterozygote, which is a viral particle having the complete genome of the rescuing virus, the antigenic genes of the pathogenic agent, and a resulting physical antigenicity which is a combination of the rescuing virus and the pathogenic agent. And fourth, there is the rescuing virus.

A vaccine containing any combination of possible expressions will immunize, provided the combination contains the expression possessing the antigenic determinants of the pathogen. In some situations, however, it may be desirable to produce a purified vaccine by selecting for that expression possessing antigenic determinants of the pathogen. For instance, government regulation may require that the purest vaccine that can be produced be used before a general use of the vaccine is allowed. In the case of vaccines produced by marker rescue, the reason for selection is that, typically, the rescuing virus is endogenous to the animal being immunized. In some animals, it has been shown that, when they are innoculated with their endogenous virus, they develop autoimmune disease. The reason for this is that, although most animals do not produce the endogenous virus, the envelope glycoprotein is expressed on the surface of the cell of many animals. Even though this envelope glycoprotein is a normal cell counterpart, animals injected with their endogenous virus produce antibodies to the endogenous virus envelope glycoprotein. The antibodies will then bind to the envelope glycoprotein on the cell surface and cause cell damage or death. Envelope glycoprotein as antigen-antibody complexes are also formed, which collect on and damage the basement membrane of the glomerulus of the animal's kidney.

Selection for the desired expression may be accomplished either by screening the resulting altered genomes to obtain the one which codes for the desired expression and allows only that genome to express itself, or by screening the desired expression from all expressions obtained. Screening of the altered genomes is done by standard hybridization techniques. Screening of all expressions obtained is done by a number of standard techniques, depending on the nature of the expression. Such techniques include but are not limited to the following examples: If the vaccine genomes are expressed as viruses, the desired expression is selected for by cell selective passage or virus selection antisera; if the expressions are other than viruses, and the determinants are surface antigens, the desired expression is selected for by surface specific antisera.

The invention is further described in connection with the following example, which is intended to illustrate the invention, but not to limit the scope thereof.

Example: Avian RNA Tumor Virus Vaccine

The production of an avian RNA tumor virus vaccine is accomplished by first identifying the antigenic and pathogenic gene regions of the exogenous oncogenic virus. The antigenic gene region is then isolated and cloned. The clones are then marker rescued from an appropriate host cell with an endogenous non-oncogenic virus. The vaccine is then purified by selecting for the genetic recombinant viral particle having the genome of the endogenous non-oncogenic virus, except that the endogenous non-oncogenic viral envelope gene has been replaced with exogenous oncogenic viral envelope gene.

Referring to FIG. 1, the oncogenic and antigenic gene regions of the genome of the avian RNA tumor virus Pr ASV (subgroup A) are identified. The genetic relationships of the different gene regions are schematically illustrated and identified. The antigenic envelope A (envA) gene region is identified, as is the oncogenic ($c^x$) gene region. Also identified are the group specific antigen (gag), reverse transcriptase (pol), and ASV-unique gene (src) gene regions. As can be seen, the envA antigenic region and the $c^x$ oncogenic region are distinct from one another. The envA region is isolated and cloned to obtain a large quantity of the gene region, (env A)$_n$. Identification of the gene regions and cloning are performed by standard techniques of hybridization and oligonucleotide mapping, and recombinant DNA cloning, respectively, as applied to the Pr ASV (subgroup A) genome by Parsons.

The cloned envA gene from the exogenous oncogenic virus is marker rescued from an appropriate host to produce the vaccine. Transfection, infection, genetic recombination, and viral replication collectively constitute marker rescue. The envA gene is introduced into a C/O cell by transfection. The transfection is performed according to the standard transfection method of Cooper and Temin, with the exception that thirty percent (30%) dimethyl sulfoxide (DMSO) is added after four (4) hours of incubation to increase the efficiency of transfection as confirmed by Cooper and Silverman for avian RNA tumor virus infected cell DNA transfection. The C/O cell is an appropriate host for the marker rescue, because it is a chicken cell which is susceptible to viruses having both the subgroup A and subgroup E envelopes, and, therefore, will allow for replication of the rescuing virus RAV-O regardless of its having the subgroup A or subgroup E envelope.

Immediately after the DMSO addition, the transfected, envA-containing, C/O cells are then infected with the rescuing, endogenous, non-oncogenic virus RAV-O. The resulting transfected, infected C/O cells which contain the cloned envA and RAV-O genome are incubated for a period of time to allow genetic recombination and viral replication to occur to produce an impure vaccine containing genetic recombinant (termed RAV-Ac$^n$ or, more appropriately, RAV-O-A), pseudotype, heterozygote, and rescuing virus, RAV-O, virus particles.

The impure vaccine is purified by selecting for the genetic recombinant RAV-Ac$^n$ virus particle. Selecting for RAV-Ac$^n$ is accomplished by standard techniques. The marker rescued C/O cells are transferred several times to obtain a high titer of the virus particles. The endogenous RAV-O virus is eliminated by cell selective infection. The virus particles are infected into C/E cells. C/E cells may not be infected with viruses having the subgroup E envelope; therefore, the RAV-O virus particles are eliminated since they have the subgroup E envelope. The resulting virus-infected C/E cells are transferred several times. The remaining virus particles are cloned by end point dilutions to eliminate the possible pseudo types. The highest dilution which retains a virus, as indicated by reverse transcriptase assay, is then passaged again. After at least six passages, the vaccine is considered to be free of potential pseudo types and heterozygotes and contains only the genetic recombinant, RAV-Ac$^n$ virus particle.

Whereas this invention is here illustrated and described with reference to one specific embodiment thereof, it is to be understood that various changes may be made in adapting the invention to different embodiments without departing from the broader inventive concepts disclosed herein and comprehended by the claims that follow.

I claim:

1. A live, non-pathogenic vaccine for a pathogenic RNA virus, comprising an immunologically effective amount of a viral, antigenic, genomic construct having an antigenic determinant region of the RNA virus, but no pathogenic properties, the viral, antigenic, genomic construct being the RAV-Ac$^n$ virus.

2. A vaccine according to claim 1, wherein the vaccine has been purified by selection for the antigenic determinant of the viral genomic construct.

3. A live, non-pathogenic, recombinant vaccine conferring immunity against the PrASV avian tumor virus in chickens, in which vaccine the PrASV env A gene has been inserted into a RAV-O virus by marker rescue to replace the endogenous envelope gene of the RAV-O virus, and the recombinant has been selected for in C/E cells.

4. A process for producing a live, non-pathogenic, recombinant vaccine conferring immunity against the PrASV avian tumor virus in chickens, comprising inserting the PrASV env A gene into a RAV-O virus by marker rescue such that said PrASV env A gene replaces the endogenous envelope gene of the RAV-O virus; and selecting for the recombinant in C/E cells.

* * * * *

UNITED STATES PATENT AND TRADEMARK OFFICE
CERTIFICATE OF CORRECTION

PATENT NO. : 5,338,674

DATED : August 16, 1994

INVENTOR(S) : Stephen E. Wright

It is certified that error appears in the above-identified patent and that said Letters Patent is hereby corrected as shown below:

Column 1, line 28, change "on" to --an--.

Signed and Sealed this

First Day of November, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,338,674
DATED : August 16, 1994
INVENTOR(S) : Stephen E. Wright

It is certified that error appears in the above-indentified patent and that said Letters Patent is hereby corrected as shown below:

Title page, item [56]:

Under "Other Publications", Page 1, Col. 2, line 6, after "AIDS" there should be added --(1988)--.

On the title page, Col. 2, first line of the "Abstract", the comma between "pathogenic" and "vaccines" should be deleted; second line, "turmor" should be changed to --tumor--; eighth line, a comma should be placed after "RAV-O".

Col. 1, line 28, under "Background of the Invention", "on" should be changed to --an--; line 37, after "as" there should be inserted --a--; line 42, "other" should be changed to --others--; Col. 2, line 44, "cross-immununity" should be changed to --cross-immunity--.

UNITED STATES PATENT AND TRADEMARK OFFICE
CERTIFICATE OF CORRECTION

PATENT NO. : 5,338,674
DATED : August 16, 1994
INVENTOR(S) : Stephen E. Wright

It is certified that error appears in the above-indentified patent and that said Letters Patent is hereby corrected as shown below:

Col. 6, lines 55 and 58, "pseudo types" should be changed to --pseudotypes--.

Signed and Sealed this

Fourth Day of July, 1995

Attest:

BRUCE LEHMAN

Attesting Officer

Commissioner of Patents and Trademarks